United States Patent
Johnson et al.

(10) Patent No.: US 12,050,212 B2
(45) Date of Patent: Jul. 30, 2024

(54) CARBON MONOXIDE SENSOR SYSTEM

(71) Applicant: GAS TECHNOLOGY INSTITUTE, Des Plaines, IL (US)

(72) Inventors: Michael Frank Johnson, Elmhurst, IL (US); Neil P. Leslie, Park Ridge, IL (US); William J. Roy, Thompson's Station, TN (US)

(73) Assignee: GAS TECHNOLOGY INSTITUTE, Des Plaines, IL (US)

( * ) Notice: Subject to any disclaimer, the term of this patent is extended or adjusted under 35 U.S.C. 154(b) by 3 days.

(21) Appl. No.: 17/717,935

(22) Filed: Apr. 11, 2022

(65) Prior Publication Data

US 2022/0326201 A1  Oct. 13, 2022

Related U.S. Application Data

(60) Provisional application No. 63/173,140, filed on Apr. 9, 2021.

(51) Int. Cl.
*G01N 33/00* (2006.01)
*G08B 21/16* (2006.01)

(52) U.S. Cl.
CPC .......... *G01N 33/004* (2013.01); *G08B 21/16* (2013.01)

(58) Field of Classification Search
CPC .................................... G01N 33/004
USPC ......................................... 73/23.2
See application file for complete search history.

(56) References Cited

U.S. PATENT DOCUMENTS

| | | | |
|---|---|---|---|
| 8,662,885 B2 | 3/2014 | Roland et al. | |
| 2010/0009304 A1* | 1/2010 | Roland | F23N 5/003 110/193 |
| 2021/0172920 A1* | 6/2021 | Hargrove | G01J 3/2803 |

FOREIGN PATENT DOCUMENTS

| | | | | |
|---|---|---|---|---|
| KR | 101842799 B1 * | 5/2018 | ........... | G01N 21/359 |
| WO | WO-2015036725 A1 * | 3/2015 | ........... | G01N 1/2258 |

OTHER PUBLICATIONS

Kim. Machine Translation of KR-101842799-B1. Published May 2018. Accessed Jun. 2023. (Year: 2018).*

* cited by examiner

*Primary Examiner* — Walter L Lindsay, Jr.
*Assistant Examiner* — Philip T Fadul
(74) *Attorney, Agent, or Firm* — Pauley Erickson & Swanson

(57) ABSTRACT

A safety system for a heating apparatus includes an inlet for receiving input gases for combustion and a flue for expelling flue gases. A carbon monoxide sensor is also included for monitoring carbon monoxide content in the heating apparatus. The safety system also includes a pressure switch which permits the input gases to mix with the flue gases based on the information from the carbon monoxide sensor.

20 Claims, 1 Drawing Sheet

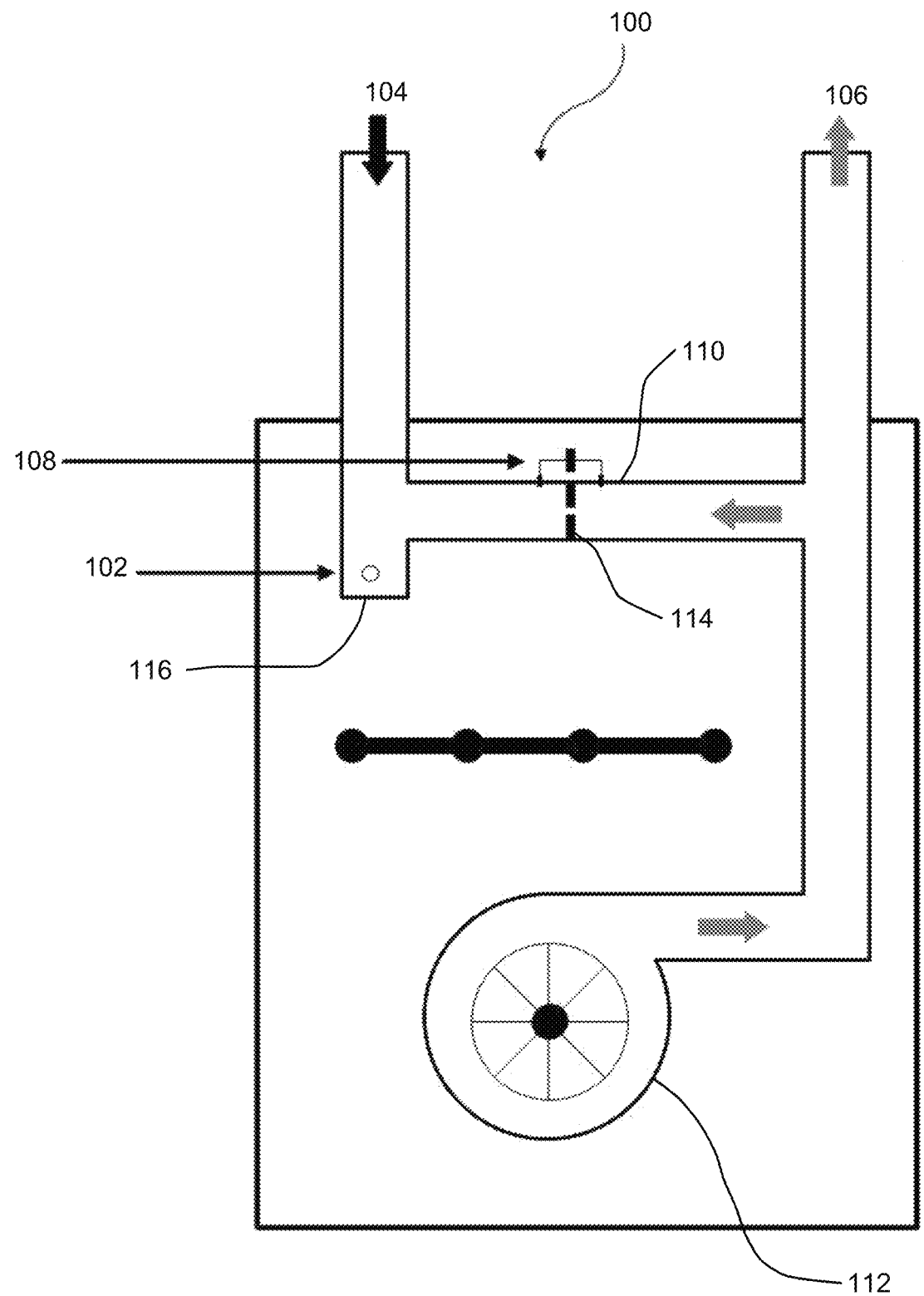

CARBON MONOXIDE SENSOR SYSTEM

CROSS REFERENCE TO RELATED APPLICATION(S)

This application claims the benefit of U.S. Provisional Application Ser. No. 63/173,140, filed on 9 Apr. 2021. The provisional application is hereby incorporated by reference herein in its entirety and is made a part hereof, including but not limited to those portions which specifically appear hereinafter.

BACKGROUND OF THE INVENTION

Field of the Invention

This invention relates generally to a carbon monoxide (CO) sensor and, more particularly, to CO sensor applications in heating systems.

Description of Related Art

Carbon monoxide (CO) forms after incomplete or partial combustion of a hydrocarbon. CO poisonous gas is the result when combustion occurs without a sufficient amount of oxygen present to react with the hydrocarbon. Heating systems that generate heat by combustion may include one or more sensors to detect a gas concentration of carbon monoxide. A controller communicates with the sensors to monitor the gas concentration to deactivate the heating system if and when deactivation is needed based on high CO content.

Current CO sensors detect gas concentration of a flue gas, therefore the sensor applications are often applied directly in a flue of a heating system. Such a location in a heating system is where ambient conditions for the sensor are extreme, therefore leading to a short sensor life.

Additionally, current systems include a pressure switch application which includes a safeguard switch that selectively permits air to enter a heating system to mix with a portion of flue gas. However, the switch application does not ensure that the air delivered for combustion is adequate for clean combustion.

Therefore, there is a continuing need for improved CO sensors that can help provide clean combustion in heating systems, while also prolonging sensor life to increase efficiency and lessen cost.

SUMMARY OF THE INVENTION

The general object of the invention can be attained, at least in part, through the application of a carbon monoxide (CO) sensor as part of a safety system for shutting off burner operation in a heating system. The safety system for a heating apparatus includes an inlet for receiving input gases for combustion, a flue for expelling flue gases, a CO sensor for monitoring CO content in the heating apparatus, and a pressure switch for permitting the input gases to mix with the flue gases.

The CO sensor is preferably positioned within a bypass circuit of the heating apparatus. The CO sensor can continuously monitor an amount of flue gas recirculation. The CO sensor can also communicate with the pressure switch to open or close a valve between the inlet and the flue. The CO sensor may be positioned within a recess between the inlet and the bypass circuit. The safety system may also include a blower for expelling flue gases out of the flue.

The general object of the invention can also be attained through a safety system for a heating apparatus with an inlet for receiving input gases for combustion and a flue for expelling flue gases. A bypass circuit is preferably positioned between the inlet and the flue. A CO sensor is also included for monitoring CO content in the heating apparatus. The CO sensor may be positioned within the bypass circuit.

The safety system may also include a pressure switch adapted to permit the input gases to mix with the flue gases. The pressure switch can also open and close the bypass circuit. The bypass circuit may include a valve between the inlet and the flue.

Other objects and advantages will be apparent to those skilled in the art from the following detailed description taken in conjunction with the appended claims and drawings.

BRIEF DESCRIPTION OF THE DRAWINGS

The FIGURE shows a schematic view of a safety system in a heating system with a CO sensor according to one embodiment of the invention.

DETAILED DESCRIPTION OF THE INVENTION

The present invention provides a CO sensor application for furnaces, boilers and water heaters. The invention identifies when a burner is operating unsafely. The invention also increases the life of CO sensors.

An operation of the invention includes shutting off burner operation for the conditions of a blocked flue, a blocked inlet and recirculation. The invention provides improved flue gas recirculation. The heating system of the invention captures recirculation within a combustion system and extends CO sensor life and reliability.

A CO sensor monitors the amount of flue gas recirculation in the heating system, ensuring that delivered air is adequate for clean combustion. The invention can identify when a vent or air inlet blockage or vent gas recirculation is occurring where the blockage is prohibiting clean combustion of a product.

The CO sensor is connected to the heating system by a bypass circuit where the CO sensor monitors the combustion performance of the unit. Here, the CO sensor sustains a longer life as the CO sensor is put in a benign environment in comparison to the overall combustion process.

The FIGURE shows a heating system 100 with a CO sensor 102 as part of a safety system according to one preferred embodiment of this invention. The heating system 100 includes a gas inlet 104 for incoming combustion gases and a flue 106 for exiting flue gases. The CO sensor 102 is preferably located inside the heating system 100 downstream from the gas inlet 104. The CO sensor 102 may be positioned inside a recess 116 as part of the components of the heating system 100. Downstream from the CO sensor 102, the heating system 100 additionally includes a pressure switch 108 for monitoring and shutting off burner operation in the system.

The pressure switch 108 is included as part of a bypass circuit 110 of the heating system 100. The bypass circuit 110 is arranged between the inlet 104 and the flue 106. The bypass circuit 110 is downstream of the CO sensor 102, thereby effectively separating the CO sensor from flue gases depending on whether the bypass circuit 112 is activated by the pressure switch 108. The bypass circuit 100 further separates the CO sensor 102 from flue gases with the aid of a valve 114. The valve 114 is part of the bypass circuit 110 and can be opened or closed as needed.

Gaseous products circulate throughout the heating system 100 with a blower 112. The blower 112 may be any conventional or commonly used blower/blower system used in heating systems. Products generated by the heating system can exit the heating system through the flue 106 and/or enter the bypass circuit 110 and contact the pressure switch 108 before reaching the CO sensor 102.

Using the CO sensor 102 and the pressure switch 108, the invention can shut off burner operation in the system 100 for the conditions of a blocked flue, Burner operation can also be shut off for a blocked inlet 104 and for recirculation. The CO sensor 102 and corresponding pressure switch 108 monitor the amount of flue gas recirculation through the heating system 100, ensuring that air delivered is adequate for clean combustion.

For example, a mixture of approximately 20-30% (preferably 22%) $O_2$ and 70-80% (preferably 78%) $N_2$ enter the heating system 100 through the gas inlet 104. However, it is to be understood that other mixtures in additional proportions may also enter the gas inlet. When flue gases exit the heating system 100 after combustion, through the flue 106, the flue gases approximately include 5-15% (preferably 9%) $CO_2$ and around 400 ppm of CO (along with some $O_2$ and $N_2$ as well). The specifics of the preferred gas content can be detected with the CO sensor 102, and also monitored with the pressure switch 108 using the bypass circuit 110.

In some embodiments of the invention, the pressure switch can also be a sensor. Other embodiments may include additional modification to the CO sensor to adjust sensor response and signal delay. Such modifications may include greater detection sensitivity in a feedback signal of the CO sensor, for example, adjusting between 100 ppm of CO and 400 ppm. A higher control signal may also be adjusted in terms of flue gas flow in the heating system. The control signal may include adjustments to a diameter for flue gas to flow through the heating system, or adjusting lengths of vent and/or air systems of the heating system.

Because the CO sensor 102 is connected by the bypass circuit 110, the CO sensor 102 also monitors the overall combustion performance of the heating system 100. Also due to placement in or near the bypass circuit 110, the overall lifespan of the CO sensor 102 is increased since the sensor 102 is not placed in the path of combustion gases directed out of the flue 106.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A safety system for a heating apparatus comprising:
    an inlet for receiving input gases for combustion;
    a flue for expelling flue gases from and after the combustion;
    a bypass circuit connecting the flue and the inlet, wherein the flue gases can pass through the bypass circuit to mix with the input gases for the combustion;
    a CO sensor in combination with the bypass circuit and configured to monitor for CO content within the input gases before the combustion; and
    a pressure switch adapted to permit the flue gases to mix into and with the input gases.

2. The safety system of claim 1 wherein the CO sensor is positioned within the bypass circuit of the heating apparatus.

3. The safety system of claim 1 wherein the CO sensor is configured to continuously monitor an amount of flue gas recirculation from the flue into the input gases for combustion.

4. The safety system of claim 1 wherein the CO sensor is adapted to communicate with the pressure switch to open or close a valve between the inlet and the flue.

5. The safety system of claim 1 wherein the CO sensor is positioned within a recess between the inlet and the bypass circuit.

6. The safety system of claim 1 wherein the gases for combustion comprise air having 20-30% oxygen and 70-80% nitrogen.

7. The safety system of claim 6 wherein the flue gases comprise 5-15% carbon dioxide.

8. The safety system of claim 7 wherein the flue gases comprise 400 ppm carbon monoxide.

9. The safety system of claim 1 further comprising a blower for expelling flue gases from combustion out of the flue.

10. The safety system of claim 1, wherein the inlet is an air inlet delivering air for combustion.

11. The safety system of claim 1, wherein the combustion occurs at a burner disposed between the inlet and the flue.

12. A safety system for a heating apparatus comprising:
    an inlet for receiving input gases for combustion;
    a flue for expelling flue gases from and after the combustion;
    a bypass circuit positioned between the inlet and the flue, wherein the flue gases can pass through the bypass circuit to mix with the input gases before the combustion; and
    a CO sensor for monitoring CO content in the input gases, wherein the CO sensor is positioned in combination with the inlet and the bypass circuit.

13. The safety system of claim 12 further comprising a pressure switch adapted to permit the input gases to mix with the flue gases.

14. The safety system of claim 13 wherein the pressure switch is configured to open and close the bypass circuit.

15. The safety system of claim 12 wherein the bypass circuit comprises a valve between the inlet and the flue.

16. The safety system of claim 12 wherein the CO sensor is positioned within a recess between the inlet and the bypass circuit.

17. The safety system of claim 10, wherein the inlet is an air inlet delivering air for combustion.

18. The safety system of claim 12, wherein the combustion occurs at a burner disposed between the inlet and the flue.

19. A safety system for a heating apparatus, the heating apparatus including a burner, an air inlet, and an exhaust flue, wherein the burner receives air for combustion through the air inlet and exhaust products from burner combustion exit through the flue, the safety system comprising:
    a bypass circuit positioned between the air inlet and the flue, wherein at least a portion of the flue gases can pass through the bypass circuit to mix with the air for combustion in the air inlet; and a CO sensor for monitoring CO content in the air for combustion, wherein the CO sensor is positioned in combination with the air inlet and the bypass circuit.

20. The safety system of claim 19 wherein the CO sensor is positioned in combination with the air inlet downstream of the bypass circuit, and the CO sensor is configured to continuously monitor an amount of flue gas recirculation through the bypass circuit from the flue into the air for combustion.

\* \* \* \* \*